United States Patent
Moszner et al.

(10) Patent No.: US 10,322,070 B2
(45) Date of Patent: Jun. 18, 2019

(54) DENTAL MATERIALS BASED ON HYBRID MONOMERS

(71) Applicant: Ivoclar Vivadent AG, Schaan (LI)

(72) Inventors: Norbert Moszner, Mauren (LI); Jörg Angermann, Sargans (CH); Urs-Karl Fischer, Arbon (CH); Martina Hauner, Feldkirch (AT)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 15/555,744

(22) PCT Filed: Feb. 11, 2016

(86) PCT No.: PCT/EP2016/052943
§ 371 (c)(1),
(2) Date: Sep. 5, 2017

(87) PCT Pub. No.: WO2016/142118
PCT Pub. Date: Sep. 15, 2016

(65) Prior Publication Data
US 2018/0042822 A1     Feb. 15, 2018

(30) Foreign Application Priority Data
Mar. 6, 2015 (EP) .................... 15158108

(51) Int. Cl.
A61K 6/083 (2006.01)
C08L 33/24 (2006.01)
A61K 6/00 (2006.01)

(52) U.S. Cl.
CPC .......... A61K 6/083 (2013.01); A61K 6/0023 (2013.01); C08L 33/24 (2013.01)

(58) Field of Classification Search
USPC ................. 523/116, 118, 120; 433/228.1
See application file for complete search history.

(56) References Cited

U.S. PATENT DOCUMENTS

| | | | |
|---|---|---|---|
| 5,741,543 A | 4/1998 | Winslow et al. | |
| 5,856,416 A * | 1/1999 | Bachmann | C08B 37/0012 526/238.23 |
| 6,057,460 A | 5/2000 | Moszner et al. | |
| 6,197,906 B1 | 3/2001 | Solomon et al. | |
| 6,916,595 B2 | 7/2005 | Fujimaki et al. | |
| 8,029,286 B2 * | 10/2011 | Craig | A61K 6/0023 106/35 |
| 8,637,611 B2 | 1/2014 | Dershem | |
| 2014/0120326 A1 | 5/2014 | Morita et al. | |

FOREIGN PATENT DOCUMENTS

JP     2001270856 A     10/2001

OTHER PUBLICATIONS

International Preliminary Report on Patentability of PCT/EP2016/052943, dated Sep. 12, 2017, 8 pages.
Peutzfeldt, A., "Resin composites in dentistry: the monomer systems," European Journal of Oral Sciences, 1997, 105: pp. 97-116, Munksgaard.
Nicholson, J. et al., "The Chemistry of Modern Dental Filling Materials," Journal of Chemical Education, Nov. 1999, vol. 76, No. 11, pp. 1497-1501.
Stansbury, J., "Curing Dental Resins and Composites by Photopolymerization," Journal of Esthetic Dentistry, vol. 12, No. 6, 2000, pp. 300-308.
Moszner, N. et al., "New Polymer-Chemical Developments in Clinical Dental Polymer Materials: Enamel-Dentin Adhesives and Restorative Composites," Journal of Polymer Science Part A: Polymer Chemistry, 2012, 50, 4369-4402, Wiley Periodicals, Inc.
Moszner, N. et al., "Chemical aspects of self-etching enamel-dentin adhesives: A systematic review," Dental Materials, 2005, 21, 895-910.
Chan, G., et al., "The Synthesis of Novel Hybrid Monomers," Aust. J. Chem., 1998, 51, 31-35.
Nie, J., et al., "Synthesis and characterization of N-isopropyl, N-methacryloxyethyl methacrylamide as a possible dental resin," Biomaterials 22 (2001) 535-540.

* cited by examiner

*Primary Examiner* — Tae H Yoon
(74) *Attorney, Agent, or Firm* — Ann M. Knab; Thad McMurray

(57) ABSTRACT

The invention relates to dental materials which contain at least one compound of Formula I

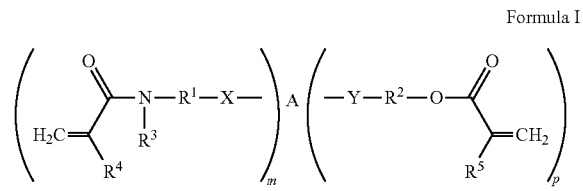

Formula I The materials are characterized by very good mechanical properties after curing.

26 Claims, No Drawings

DENTAL MATERIALS BASED ON HYBRID MONOMERS

CROSS-REFERENCE TO RELATED APPLICATIONS

This application is a National Stage application of International patent application PCT/EP2016/052943 filed on Feb. 11, 2016, which claims priority to European patent application No. 15158108.9 filed on Mar. 6, 2015, the disclosures of which are incorporated herein by reference in their entirety.

FIELD OF THE INVENTION

The present invention relates to thermally and/or light-curing dental materials with very good mechanical properties which are particularly suitable as dental filling composites and as material for inlays, onlays, crowns, bridges or veneering materials.

BACKGROUND OF THE INVENTION

The polymerizable organic matrix of dental filling composites and adhesives is usually based on a mixture of dimethacrylates (cf. A. Peutzfeldt, Resin composites in dentistry: the monomer systems, Eur. J. Oral. Sci. 105 (1997) 97-116; J. W. Nicolson, H. M. Anstice, The chemistry of modern dental filling materials, J. Chem. Ed. 76 (1999) 1497-1501; J. W. Stansburry, Curing dental resins and composites by photopolymerization, J. Esthet. Dent., 12 (2000) 300-308; N. Moszner, T. Hirt, New Polymer-Chemical Developments in Clinical Dental Polymer Materials: Enamel-Dentin Adhesives and Restorative Composites, J. Polym. Sci. Part A: Polym. Chem. 50 (2012) 4369-4402). Examples of frequently used dimethacrylates are the highly viscous crosslinkers 2,2-bis[4-(2-hydroxy-3-methacryloyloxypropyl)phenyl]propane (bis-GMA) and 1,6-bis-[2-methacryloyloxyethoxycarbonylamino]-2,4,4-trimethylhexane (UDMA) or the low-viscosity dimethacrylates used as diluting monomers, such as e.g. bis(methacryloyloxymethyl)tricyclo[5.2.1.]decane (TCDMA), decanediol-1,10-dimethacrylate ($D_3MA$) and triethylene glycol dimethacrylate (TEGDMA). Bisacrylamides, such as e.g. N,N'-diethyl-1,3-bis(acrylamido)-propane, which are characterized under aqueous-acid conditions by significantly higher hydrolytic stability compared with dimethacrylates (cf. N. Moszner, U. Salz, J. Zimmermann, Dent. Mater. 21 (2005) 895-910), are also suitable as crosslinkers for aqueous adhesives.

Monomers which contain two different polymerizable groups are called hybrid monomers. EP 0 792 882 A1 discloses dental materials which contain polymerizable hybrid monomers which, in addition to norbornenyl or norbornadienyl groups, also have (meth)acrylate, vinyl, allyl, allyl ether, vinyl ether, epoxy or styryl groups. These monomers can be polymerized by different mechanisms, with the result that a multistage polymerization, the combination of different polymerization mechanisms or the synthesis of polymerizable polymers is possible.

Chan et al., Austr. J. Chem. 51 (1998) 31-35 describe the synthesis of hybrid monomers which contain both (meth)acrylamide and also (meth)acrylate groups. These monomers are intended to be suitable as crosslinkers when solubility both in organic and also in aqueous systems is required or when the presence of an easily hydrolyzable group is desired for the controlled degradation of the polymer network.

EP 1 182 033 A1 discloses materials for image recording which can contain a polymeric binder with different radically polymerizable groups.

JP 2001270856 A discloses a method for preparing N-(meth)-acryloyloxyethylacrylamides by transesterification. The method is intended to produce the desired products at high yield and purity.

WO 2010/019832 discloses amide-extended maleic acid imides which are intended to be suitable for strengthening thermally curing adhesives without impairing their heat stability. By "amide-extended" is meant compounds which contain at least one amide group in a non-terminal position of the molecule.

WO 96/24644 A1 relates to pressure-sensitive adhesives which are said to be suitable for coating articles. The adhesives can contain polyunsaturated monomers the unsaturated groups of which have different reactivities. Premature gelling is said to be prevented by the different reactivities.

WO 98/01419 discloses gels for gel electrophoresis which contain asymmetric crosslinkers. These are molecules with two differently reactive vinyl groups. By means of the reaction of the more reactive groups, linear polymer chains are to be formed first which are then crosslinked with each other via the second group, with the result that gels are formed with a microporous structure which is advantageous for the separation of biomolecules.

SUMMARY OF THE INVENTION

The object of the invention is to provide dental materials which are characterized by improved mechanical properties compared with dental materials based on dimethacrylates.

DETAILED DESCRIPTION

The object is achieved according to the invention by dental materials which contain at least one radically polymerizable compound according to general formula I:

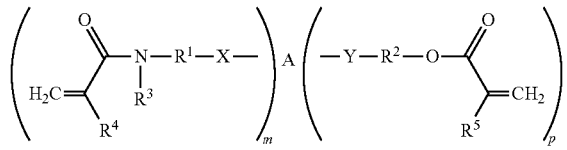

Formula I in which the variables have the following meanings:
  A is an aliphatic linear or branched $C_1$-$C_{20}$ hydrocarbon radical which can be interrupted by one or more O or S and/or can carry one or more OH side groups,
  X, Y independently of each other in each case are absent or are —COO—, —CON($R^6$)—, —CO—NH—CO or —NH—CO—O—,
  $R^1$, $R^2$ independently of each other in each case are absent or are an aliphatic linear or branched $C_1$-$C_{10}$ alkylene radical which can be interrupted by one or more O or S, wherein A, $R^1$ and $R^2$ together contain at least 3 C atoms and wherein $R^1$ and X as well as $R^2$ and Y are preferably not absent at the same time,
  $R^3$ is an aliphatic linear or branched $C_1$-$C_5$ alkyl radical,
  $R^4$, $R^5$ independently of each other in each case are hydrogen or an aliphatic linear $C_1$-$C_6$ alkyl radical, $R^6$ is hydrogen or an aliphatic linear $C_1$-$C_8$ alkyl radical, and m, p independently of each other in each case are an integer from 1 to 3.

In the compounds of Formula I, A is an m+p-valent radical to which in each case m acrylamide groups (left-hand bracket term) and p acrylate groups (right-hand bracket term) are bonded. These are hybrid monomers which have 2 to 6, preferably 2 to 3, radically polymerizable groups.

The grouping —$R^1$—X-A-Y—$R^2$— forms a spacer which joins the polymerizable acrylamide group(s) to the polymerizable acrylate group(s). Compounds with a linear spacer are preferred, i.e. the at least 3 C atoms of the A, $R^1$ and $R^2$ radicals are preferably arranged linearly. Likewise, $R^1$, $R^2$ and A are preferably linear groups. Compounds of Formula (I) in which at least one of the radicals X and Y is —NH—CO—O— are particularly preferred.

Formula I extends only to those compounds which are compatible with the theory of chemical valence. For example, the sum of m and p, when A is a $C_1$ radical, can at most be 4. The indication that a radical is interrupted by one or more O atoms, S atoms etc. is to be understood to mean that these groups are inserted in each case into the carbon chain of the radical. These groups are thus bordered on both sides by C atoms and cannot be terminal. $C_1$ radicals cannot be interrupted.

It was surprisingly found that, in the case of radical polymerization, compounds of Formula I produce materials which are characterized by significantly improved mechanical properties vis-à-vis materials with conventional dental crosslinkers.

Compounds of Formula I are preferred in which the variables have the following meanings:

A is an aliphatic linear or branched $C_1$-$C_{15}$ hydrocarbon radical which can be interrupted by one or more O;

X, Y independently of each other in each case are absent or are —NH—CO—O—, wherein X and Y are preferably not absent at the same time, $R^1$, $R^2$ independently of each other in each case are absent or are an aliphatic linear or branched $C_1$-$C_{10}$ alkylene radical which can be interrupted by one or more O, wherein A, $R^1$ and $R^2$ together contain at least 3 C atoms, $R^3$ is an aliphatic linear $C_1$-$C_3$ alkyl radical, $R^4$, $R^5$ independently of each other in each case are hydrogen, methyl or ethyl, and m, p independently of each other in each case are an integer from 1 to 3.

Compounds are particularly preferred in which the variables of Formula I have the following meanings:

A is an aliphatic branched, preferably linear $C_1$-$C_8$ hydrocarbon radical which can be interrupted by one or more O, X is —NH—CO—O— or is preferably absent, Y is absent or preferably is —NH—CO—O—, wherein X and Y are preferably not dispensed with at the same time, $R^1$ is absent, $R^2$ is absent or is an aliphatic linear $C_1$-$C_2$ alkylene radical, $R^3$ is methyl or ethyl, $R^4$, $R^5$ independently of each other are hydrogen or methyl, and m, p independently of each other in each case are 1 or 2.

Some of the compounds of general formula I are known from the state of the art and can be prepared using simple synthesis methods. For example, (m+p)-functional α,ω-aminoalcohols can be reacted with α,β-unsaturated carboxylic acid chlorides in the presence of an auxiliary base to form di- or higher-functionalized hybrid monomers of general formula I, general example:

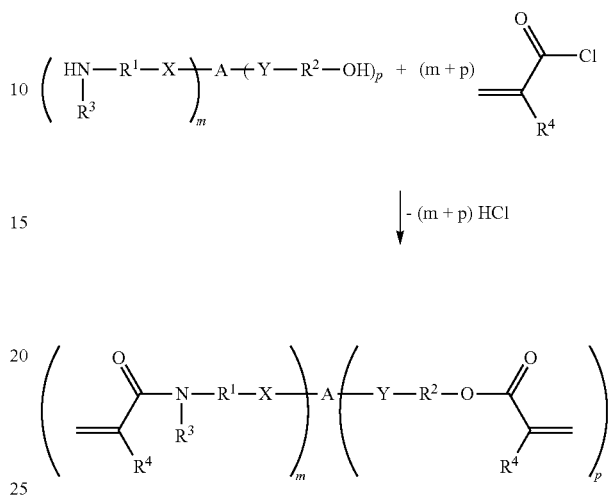

A specific example is:

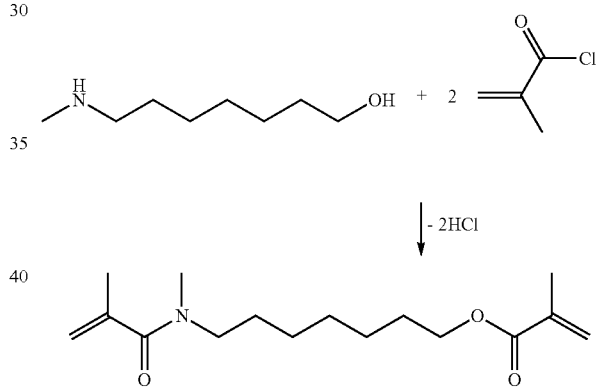

As a result of the greater nucleophilicity of amino groups in comparison with OH groups, the introduction of the different polymerizable (meth)acrylamide and (meth)acrylate groups can also take place in stages. For example, the (m+p)-functional α,ω-aminoalcohol is reacted first with the α,β-unsaturated carboxylic acid chloride $CH_2$=$CHR^4$—COCl at low temperature and then acylated at room temperature with the α,β-unsaturated carboxylic acid chloride $CH_2$=$CHR^5$—COCl:

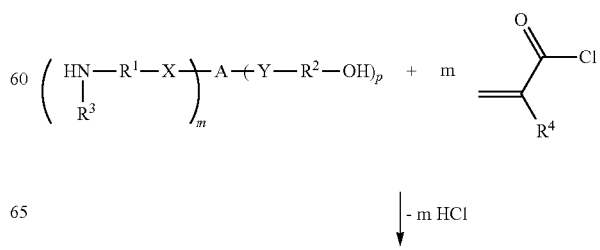

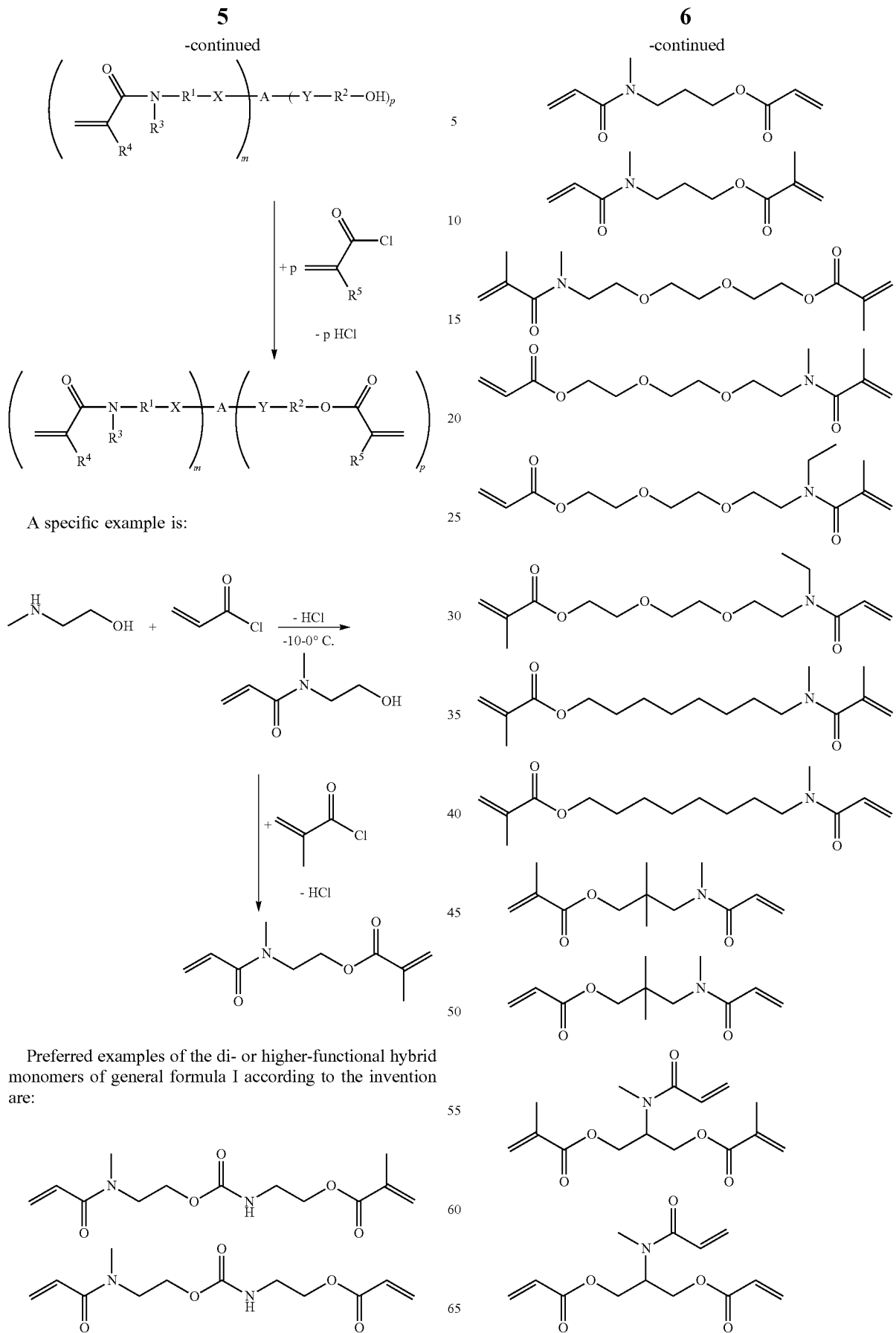
A specific example is:
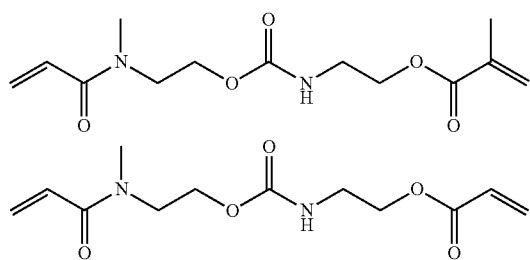
Preferred examples of the di- or higher-functional hybrid monomers of general formula I according to the invention are:
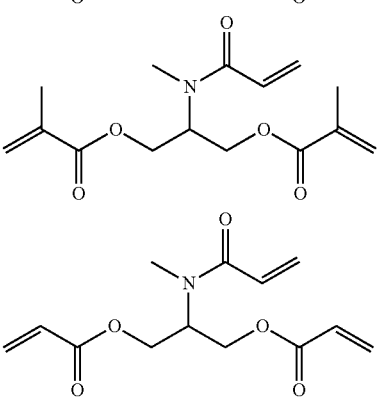

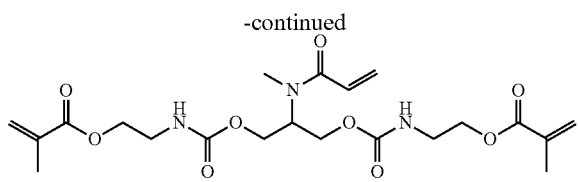

In addition to the monomers of general formula I the dental materials according to the invention preferably additionally contain further radically polymerizable monomers, in particular mono- and/or polyfunctional (meth)acrylic acid derivatives. Materials are particularly preferred which contain at least one multifunctional (meth)acrylate or a mixture of mono- and multifunctional (meth)acrylates as radically polymerizable monomer. By monofunctional (meth)acrylates is meant compounds with one, by polyfunctional (meth)acrylates compounds with two or more, preferably 2 to 4, radically polymerizable groups. According to a quite particularly preferred embodiment, the compositions according to the invention contain at least one dimethacrylate or a mixture of mono- and dimethacrylates. Materials which contain mono- and multifunctional (meth)acrylates as radically polymerizable monomer are particularly suitable as dental materials. In all cases, methacrylates are preferred as comonomers. It was found that the monomers of Formula I and in particular the preferred compounds of Formula I with the comonomers named here have good compatibility and form homogeneous mixtures which, upon polymerization, produce materials with very good mechanical properties. Compounds of Formula I which are liquid under standard conditions are preferred.

Preferred mono- or polyfunctional methacrylates are methyl, ethyl, hydroxyethyl, butyl, benzyl, tetrahydrofurfuryl or isobornyl (meth)acrylate, p-cumyl-phenoxyethylene glycol methacrylate (CMP-1E), bisphenol A di(meth)acrylate, bis-GMA (an addition product of methacrylic acid and bisphenol A diglycidyl ether), UDMA (an addition product of 2-hydroxyethyl methacrylate (HEMA) and 2,2,4-trimethyl hexamethylene diisocyanate), TMX-UDMA (an addition product of a mixture of HEMA and hydroxypropyl methacrylate (HPMA) with α,α,α',α'-tetramethyl-m-xylylene diisocyanate (TMXDI)), bis(methacryloyloxymethyl) tricyclo[5.2.1.]decane (TCDMA), ethoxylated or propoxylated bisphenol A di(meth)acrylate, such as e.g. the bisphenol A dimethacrylate 2-[4-(3-methacryloyloxy-ethoxyethyl)phenyl]-2-[4-(3-methacryloyloxyethyl)phenyl]-propane) (SR-348c) with 3 ethoxy groups or 2,2-bis[4-(2-(meth)acryloxypropoxy)phenyl]propane, di-, tri- or tetraethylene glycol di(meth)acrylate, trimethylolpropane tri(meth)acrylate, pentaerythritol tetra-(meth)acrylate, as well as glycerol di(meth)acrylate, 1,4-butanediol di(meth)acrylate, 1,10-decanediol di(meth)acrylate or 1,12-dodecanediol di(meth)acrylate or glycerol trimethacrylate (GTMA).

N-mono- or -disubstituted acrylamides, such as e.g. N-ethyl acrylamide, N,N-dimethyl acrylamide, N-(2-hydroxyethyl)acrylamide or N-methyl-N-(2-hydroxyethyl) acrylamide, or N-monosubstituted methacrylamides, such as e.g. N-ethylmethacrylamide or N-(2-hydroxyethyl)methacrylamide as well as N-vinylpyrrolidone are further preferred. These monomers are characterized by a low viscosity and a high hydrolytic stability and are particularly suitable as diluting monomers.

Crosslinking pyrrolidones, such as e.g. 1,6-bis(3-vinyl-2-pyrrolidonyl)-hexane or commercially available bisacrylamides, such as methylene- or ethylenebisacrylamide, or bis-(meth)acrylamides, such as e.g. N,N'-diethyl-1,3-bis(acrylamido)-propane, 1,3-bis(methacrylamido)-propane, 1,4-bis(acrylamido)-butane or 1,4-bis(acryloyl)piperazine, which can be synthesized by reaction from the corresponding diamines with (meth)acrylic acid chloride, are also preferred. These monomers are characterized by a high hydrolytic stability and are particularly suitable as crosslinking monomers.

Particularly preferred comonomers are: CMP-1E, bis-GMA, UDMA, TMX-UDMA, TCDMA, ethoxylated or propoxylated bisphenol A dimethacrylate, SR-348c, triethylene glycol dimethacrylate, glycerol dimethacrylate, 1,10-decanediol dimethacrylate or glycerol trimethacrylate (GTMA) as well as N,N'-diethyl-1,3-bis(acrylamido)-propane.

Alternatively or in addition, the dental materials according to the invention can contain, in addition to the comonomers named above, one or more acid-group-containing radically polymerizable monomers (adhesive monomers) as additional monomers. These give the materials self-adhesive and/or self-etching properties.

Preferred acid-group-containing monomers are polymerizable carboxylic acids, phosphonic acids, phosphoric acid esters and sulphonic acids.

Preferred carboxylic acids are maleic acid, acrylic acid, methacrylic acid, 2-(hydroxymethyl)acrylic acid, 4-(meth) acryloyloxyethyltrimellitic acid, 10-methacryloyloxydecylmalonic acid, N-(2-hydroxy-3-methacryloyloxypropyl)-N-phenylglycine and 4-vinylbenzoic acid.

Preferred phosphonic acid monomers are vinyl phosphonic acid, 4-vinylphenyl phosphonic acid, 4-vinylbenzyl phosphonic acid, 2-methacryloyloxyethyl phosphonic acid, 2-methacrylamidoethyl phosphonic acid, 4-methacrylamido-4-methylpentylphosphonic acid, 2-[4-(dihydroxyphosphoryl)-2-oxa-butyl]acrylic acid or 2-[4-(dihydroxyphosphoryl)-2-oxa-butyl]acrylic acid ethyl and -2,4,6-trimethyl phenyl ester.

Preferred acidic polymerizable phosphoric acid esters are 2-methacryloyloxypropyl mono- or dihydrogen phosphate, 2-methacryloyloxyethyl mono- or dihydrogen phosphate, 2-methacryloyloxyethylphenyl hydrogen phosphate, dipentaerythritol penta-methacryloyloxy phosphate, 10-methacryloyloxydecyl dihydrogen phosphate, phosphoric acid mono-(1-acryloyl-piperidin-4-yl) ester, 6-(methacrylamido) hexyl dihydrogen phosphate and 1,3-bis-(N-acryloyl-N-propyl-amino)-propan-2-yl dihydrogen phosphate.

Preferred polymerizable sulphonic acids are vinyl sulphonic acid, 4-vinylphenyl sulphonic acid or 3-(methacrylamido)propyl sulphonic acid.

Particularly preferred acid monomers are 4-(meth)acryloyloxyethyltrimellitic acid anhydride, 10-methacryloyloxydecylmalonic acid, 2-methacryloyloxyethyl phosphonic acid, 2-methacrylamidoethyl phosphonic acid, 2-[4-(dihydroxyphosphoryl)-2-oxa-butyl]acrylic acid, 2-[4-(dihydroxyphosphoryl)-2-oxa-butyl]acrylic acid ethyl or -2,4,6-trimethyl phenyl ester, 2-methacryloyloxypropyl mono- or dihydrogen phosphate, 2-methacryloyloxyethyl mono- or dihydrogen phosphate, 2-methacryloyloxyethylphenyl hydrogen phosphate, 10-methacryloyloxydecyl dihydrogen phosphate, 6-(methacrylamido)hexyl dihydrogen phosphate and 1,3-bis-(N-acryloyl-N-propyl-amino)-propan-2-yl dihydrogen phosphate.

The dental materials according to the invention preferably also contain an initiator for the radical polymerization.

Benzophenone, benzoin and derivatives thereof or α-diketones or derivatives thereof, such as 9,10-phenanthrenequinone, 1-phenyl-propane-1,2-dione, diacetyl or 4,4'-dichlorobenzil are preferred for the initiation of the radical photopolymerization. Camphorquinone and 2,2-dimethoxy-2-phenyl-acetophenone are particularly preferably used and α-diketones in combination with amines as reducing agent, such as e.g. 4-(dimethylamino)benzoic acid ethyl ester, N,N-dimethylaminoethyl methacrylate, N,N-dimethyl-sym.-xylidine or triethanolamine are particularly preferably used. Norrish type I photoinitiators, above all acyl- or bisacylphosphine oxides, monoacyltrialkyl or diacyldialkyl germanium compounds, such as e.g. benzoyltrimethylgermanium, dibenzoyldiethylgermanium or bis(4-methoxybenzoyl)diethylgermanium are also particularly suitable. Advantageously, mixtures of the different photoinitiators can also be used, such as e.g. dibenzoyldiethylgermanium in combination with camphorquinone and 4-dimethylaminobenzoic acid ethyl ester.

Redox-initiator combinations, such as e.g. combinations of benzoyl peroxide with N,N-dimethyl-sym.-xylidine or N,N-dimethyl-p-toluidine are preferably used as initiators for a polymerization carried out at room temperature. In addition, redox systems consisting of peroxides or hyperoxides and reducing agents, such as e.g. ascorbic acid, barbiturates, thioureas or sulphinic acids, are also particularly suitable.

Furthermore, the dental materials according to the invention preferably also contain at least one organic or particularly preferably inorganic particulate filler. Fillers based on oxides are preferred, such as $SiO_2$, $ZrO_2$ and $TiO_2$ or mixed oxides of $SiO_2$, $ZrO_2$, ZnO and/or $TiO_2$, nanoparticulate or microfine fillers such as pyrogenic silicic acid or precipitated silicic acid (weight-average particle size of from 10-1,000 nm) as well as mini fillers, such as quartz, glass ceramic or X-ray opaque glass powder of e.g. barium or strontium aluminium silicate glasses (weight-average particle size of from 0.2-10 μm). Further preferred fillers are X-ray opaque fillers, such as ytterbium trifluoride or nanoparticulate tantalum(V) oxide or barium sulphate or mixed oxides of $SiO_2$ with ytterbium(III) oxide or tantalum(V) oxide (weight-average particle size of from 10-1,000 nm).

To improve the bond between the filler particles and the crosslinked polymerization matrix, $SiO_2$-based fillers can be surface-modified with methacrylate-functionalized silanes, such as e.g. 3-methacryloyloxypropyltrimethoxysilane. For the surface-modification of non-silicate fillers, e.g. of $ZrO_2$ or $TiO_2$, functionalized acidic phosphates, such as e.g. 10-methacryloyloxy dihydrogen phosphate can also be used.

Depending on the desired intended use, the dental materials according to the invention can preferably also contain a solvent, in particular water, ethanol or a mixture thereof.

Optionally, the compositions used according to the invention can also contain further additives, above all stabilizers, such as e.g. polymerization stabilizers, flavourings, dyes, microbiocidal active ingredients, fluoride-ion-releasing additives, optical brighteners, fluorescent agents, plasticizers and/or UV absorbers.

According to the invention, those dental materials which contain the following components are preferred:
 a) 0.1 to 50 wt.-%, preferably 1 to 40 wt.-% and particularly preferably 2 to 30 wt.-% of at least one compound of general formula I,
 b) 0.01 to 10 wt.-%, particularly preferably 0.1 to 3.0 wt.-% of at least one initiator, and optionally
 c) 0 to 80 wt.-%, preferably 0 to 60 wt.-% and particularly preferably 5 to 50 wt.-% other monomer(s), and optionally
 d) 0 to 80 wt.-% filler(s), and optionally
 e) 0 to 70 wt.-% solvent.

Dental materials for use as cement or filling composite preferably have the following composition:
 a) 0.1 to 40 wt.-%, preferably 1 to 30 wt.-% and particularly preferably 5 to 30 wt.-% of at least one compound of general formula I,
 b) 0.01 to 10 wt.-%, particularly preferably 0.1 to 3.0 wt.-% of at least one initiator,
 c) 0 to 50 wt.-%, preferably 0 to 40 wt.-% and particularly preferably 5 to 40 wt.-% other monomer(s),
 d) 10 to 80 wt.-%, preferably 20 to 80 wt.-%, particularly preferably 30 to 80 wt.-% filler(s).

Dental materials for use as adhesives or coating material preferably have the following composition:
 a) 0.1 to 50 wt.-%, preferably 1 to 40 wt.-% and particularly preferably 2 to 30 wt.-% of at least one compound of general formula I,
 b) 0.01 to 10 wt.-%, particularly preferably 0.1 to 3.0 wt.-% of at least one initiator,
 c) 0 to 80 wt.-%, preferably 5 to 60 wt.-% and particularly preferably 5 to 50 wt.-% other monomer(s),
 d) 0 to 20 wt.-% filler(s),
 e) 0 to 70 wt.-%, preferably 0 to 60 wt.-% and particularly preferably 0 to 50 wt.-% solvents, in particular water and/or ethanol.

Dental materials for the manufacture of prostheses or artificial teeth preferably have the following composition:
 a) 0.1 to 50 wt.-%, preferably 1 to 40 wt.-% and particularly preferably 2 to 30 wt.-% of at least one compound of general formula I,
 b) 0.01 to 10 wt.-%, particularly preferably 0.1 to 3.0 wt.-% of at least one initiator, and
 c) 0 to 80 wt.-%, preferably 0 to 60 wt.-% and particularly preferably 5 to 50 wt.-% other monomer(s), and
 d) 0 to 40 wt.-% filler(s).

Dental materials for the manufacture of inlays, onlays, crowns or bridges preferably have the following composition:
 a) 0.1 to 50 wt.-%, preferably 1 to 40 wt.-% and particularly preferably 2 to 30 wt.-% of at least one compound of general formula I,
 b) 0.01 to 10 wt.-%, particularly preferably 0.1 to 3.0 wt.-% of at least one initiator, and optionally
 c) 0 to 60 wt.-%, preferably 0 to 50 wt.-% and particularly preferably 5 to 50 wt.-% other monomer(s), and optionally
 d) 10 to 80 wt.-%, preferably 15 to 80 wt.-% and particularly preferably 20 to 80 wt.-% filler(s).

Unless otherwise stated, all quantities relate to the total mass of the materials. The individual quantity ranges can be chosen separately.

Those materials which consist of the named components are particularly preferred. Furthermore, those materials are preferred in which the individual components are in each case selected from the above-named preferred and particularly preferred substances.

The materials according to the invention are particularly suitable as dental materials, in particular as dental adhesives, cements, filling composites and veneering materials, and as materials for the manufacture of prostheses, artificial teeth, inlays, onlays, crowns and bridges. They are characterized vis-à-vis materials based on dimethacrylates by significantly improved mechanical properties (flexural strength and modulus of elasticity).

The dental materials are suitable primarily for intraoral application by the dentist to restore damaged teeth (clinical materials), e.g. as dental cements, filling composites and veneering materials. However, they can also be used extraorally, for example in the manufacture or repair of dental restorations, such as prostheses, artificial teeth, inlays, onlays, crowns and bridges (technical materials).

The invention is explained in more detail below by means of embodiment examples.

EXAMPLES

Example 1

Synthesis of 2-{[(2-(N-methylacrylamido)-ethoxy)-carbonyl]-amino}-ethyl methacrylate (MAMMA)

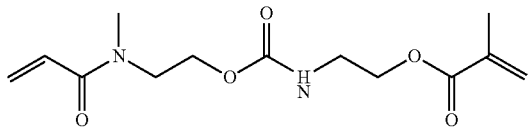 [SMILES: C=CC(=O)N(C)CCOC(=O)NCCOC(=O)C(=C)C]

25.4 g (0.164 mol) 2-isocyanatoethyl methacrylate was added dropwise over a period of 30 min to a solution of 15.2 mg bismuth(III)neodecanoate and 8.5 mg BHT in 21.2 g (0.164 mol) N-(2-hydroxyethyl)-N-methyl-acrylamide. The reaction mixture warmed up to approx. 56° C. and was then stirred at 50° C. bath temperature. The course of the reaction was followed using IR spectroscopy and titration. After 11 h at 50° C., 44.8 g (96% theoretical) MAMMA was obtained as a clear, colourless liquid with a purity of 96.95% (HPLC). $n_D^{20}$=1.4990; η (23° C.)=1.84 Pa·s $^1$H-NMR (400 MHz, CDCl$_3$): 2 rotamers (approx. 1:1), δ (ppm)=1.94 (s, 3H, C$\underline{H}_{3,methacryl}$) 3.03 and 3.13 (2 s, in each case 1.5H, NCH$_3$), 3.48 (q, J=5.6 Hz, 2H, HN—C$\underline{H}_2$), 3.63 and 3.68 (2 t, in each case J=5.7 Hz, in each case 1H, H$_3$CN—C$\underline{H}_2$), 4.19-4.26 (m, 4H, OCH$_2$), 5.40 (s, 1H, NH), 5.60 and 6.12 (2 s, in each case 1H, C=C$\underline{H}_2$), 5.65-5.72, 6.29-6.34 and 6.55-6.62 (3 m, in each case 1H, $\underline{H}$C=C$\underline{H}_2$).

$^{13}$C-NMR (100 MHz, CDCl$_3$): 2 rotamers (approx. 1:1), δ (ppm)=18.3 (CH$_{3, methacryl}$) 34.1 and 36.5 (NCH$_3$), 40.1 and 40.2 (HN—C$\underline{H}_2$), 47.4 and 48.8 (NCH$_2$), 61.8, 62.3, 63.5 and 63.6 (OCH$_2$), 126.0 and 126.1 (C=$\underline{C}$H$_2$), 127.3 and 127.5 (H$\underline{C}$=CH$_2$), 128.0 and 128.2 (HC=$\underline{C}$H$_2$), 135.9 ($\underline{C}$=CH$_2$), 156.0 and 156.3 (C=O$_{urethane}$), 166.6 and 166.8 (C=O$_{amide}$) 167.2 (C=O$_{ester}$).

IR (diamond ATR):ν (cm$^{-1}$)=3299 (m, NH), 2955 (m, CH$_2$, CH$_3$), 1712 (vs, C=O$_{ester}$), 1645 (s, C=O$_{amide}$), 1610 (s, C=C), 1532 (s, NH), 1451 (s, CH$_2$, CH$_3$), 1251 (s, C—N), 1153 (vs, COC), 948 (s, =CH).

Example 2

Polymerization Resins Based on MAMMA from Example 1

Monomer mixtures (resins) A to D (proportions in wt.-%) were prepared by mixing UDMA, camphorquinone (CQ), 4-(dimethyl-amino)benzoic acid ethyl ester (EDMAB) with the highly viscous monomers TMX-UDMA (an addition product of a mixture of HEMA and hydroxypropyl methacrylate (HPMA) with α,α,α',α'-tetra-methyl-m-xylylene diisocyanate) or TCM-UDMA (reaction product of 1 mol 4,8-bis(hydroxymethyl)tricyclo[5.2.1.0(2,6)]decane with 2 mol 2-isocyanatoethyl methacrylate) and the diluting monomers MAMMA from Example 1 or glycerol trimethacrylate (GTMA) (Table 1):

TABLE 1

Radically polymerizable monomer mixtures

| Components | Resin A | Resin B | Resin C*) | Resin D*) | Resin E**) |
|---|---|---|---|---|---|
| UDMA | 52.58 | 52.58 | 52.58 | 52.58 | 52.58 |
| TMX-UDMA | 14.88 | — | 14.88 | — | — |
| TCM-UDMA | — | 14.88 | — | 14.88 | — |
| bisGMA | — | — | — | — | 14.88 |
| MAMMA | 31.74 | 31.74 | — | — | — |
| GTMA | — | — | 31.74 | 31.74 | — |
| TEGDMA | — | — | — | — | 31.74 |
| CQ | 0.30 | 0.30 | 0.30 | 0.30 | 0.30 |
| EDMAB | 0.50 | 0.50 | 0.50 | 0.50 | 0.50 |

*)comparison example
**)commercial resin, comparison example

Test pieces were prepared from the resins (dimensions 2×2×25 mm), which were irradiated for 2×3 minutes with a dental light source (Spectramat®, Ivoclar Vivadent AG) and thus cured. The flexural strength and the flexural modulus of elasticity were determined according to ISO standard 4049 (Dentistry—Polymer-based filling, restorative and luting materials) (Table 2).

TABLE 2

Mechanical properties of the cured resins

| Property | Resin A | Resin B | Resin C*) | Resin D*) | Resin E*) |
|---|---|---|---|---|---|
| Flexural strength (MPa) | 105.1 ± 2.3 | 109.0 ± 2.2 | 59.9 ± 5.8 | 56.5 ± 8.9 | 63.3 ± 1.4 |
| Flexural modulus of elasticity (GPa) | 2.45 ± 0.09 | 2.49 ± 0.23 | 1.49 ± 0.06 | 2.01 ± 0.10 | 1.89 ± 0.13 |

*)comparison example

The results prove the very good mechanical properties of polymers with the monomer MAMMA according to the invention as diluting monomer, also compared with the trifunctional diluting monomer GTMA. A usual dental resin with an analogous composition (Resin E), in which, on the one hand, the highly viscous dimethacrylate bis-GMA and, on the other hand, the diluting monomer TEGDMA were used, produced polymers with significantly poorer mechanical properties.

Example 3

Composite Cement Based on MAMMA from Example 1

The following composite cement pastes were prepared with a three roll mill (proportions in wt.-%) (Table 3):

TABLE 3

Compositions of dental cements

| Component | Cement A | Cement B*) |
|---|---|---|
| UDMA | 35.67 | 35.67 |
| MAMMA | 8.83 | — |
| D₃MA | — | 8.83 |
| CQ | 0.27 | 0.27 |
| EDMAB | 0.26 | 0.26 |
| Ox-50¹⁾ | 37.83 | 37.83 |
| YbF₃²⁾ | 17.14 | 17.14 |

*)comparison example
¹⁾silanized pyrogenic silicic acid (Degussa) with a primary particle size of 40 nm
²⁾ytterbium trifluoride (Auer Remy) with an average particle size of 0.2 µm Test pieces were prepared from the cement pastes (dimensions 2×2×25 mm), which were cured for 2×3 minutes with a dental light source (Spectramat®, Ivoclar Vivadent AG). The flexural strength and the flexural modulus of elasticity were determined according to ISO standard 4049 (Dentistry—Polymer-based filling, restorative and luting materials) (Table 4). The results prove the very good mechanical properties of the cement with the monomer MAMMA according to the invention as diluting monomer compared with the cement with the usual dental diluting monomer D₃MA.

TABLE 4

Mechanical properties of the cured resins

| Property | Cement A | Cement B*) |
|---|---|---|
| Flexural strength (MPa) | 114.9 ± 6.9 | 89.0 ± 10.2 |
| Flexural modulus of elasticity (GPa) | 6.04 ± 0.21 | 4.38 ± 0.29 |

*)comparison example

Example 4

Filling Composite Based on MAMMA from Example 1

Composites A and B were prepared in a Linden kneader (Table 5):

TABLE 5

Composition of filling composites

| Component | Composite A | Composite B*) | Composite C*) |
|---|---|---|---|
| Bis-GMA | 11.85 | 11.85 | 11.85 |
| UDMA | 4.33 | 4.33 | 4.33 |
| MAMMA | 5.66 | — | — |
| TEGDMA | — | 5.66 | — |
| Bisacrylamide⁵⁾ | — | — | 5.66 |
| CQ | 0.09 | 0.09 | 0.09 |
| EDMAB | 0.11 | 0.11 | 0.11 |
| Ox-50¹⁾ | 10.87 | 10.87 | 10.87 |
| YbF₃²⁾ | 14.62 | 14.62 | 14.62 |
| Spherosil³⁾ | 8.60 | 8.60 | 8.60 |
| Glass filler⁴⁾ | 43.87 | 43.87 | 43.87 |

*)comparison example
**)commercial filling composite, comparison example
¹⁾silanized pyrogenic silicic acid (Degussa) with a primary particle size of 40 nm
²⁾ytterbium trifluoride (Auer Remy) with an average particle size of 0.2 µm
³⁾silanized SiO₂—ZrO₂ mixed oxide (Tokuyama Soda) with an average particle size of 1.2 µm
⁴⁾silanized Al-borosilicate glass (Schott) with an average particle size of 0.7 µm
⁵⁾N,N-diethyl-1,3-bis(acrylamidopropane)

Test pieces were prepared from the composite pastes (dimensions 2×2×25 mm), which were cured for 2×3 minutes with a dental light source (Spectramat®, Ivoclar Vivadent AG). The flexural strength and the flexural modulus of elasticity were determined according to ISO standard 4049 (Dentistry—Polymer-based filling, restorative and luting materials) (Table 6).

TABLE 6

Mechanical properties of cured composites

| Property | Composite A | Composite B*) | Composite C*) |
|---|---|---|---|
| Flexural strength (MPa) | 140.9 ± 7.6 | 116.5 ± 12.2 | 120.2 ± 14.9 |
| Flexural modulus of elasticity (GPa) | 8.47 ± 0.40 | 6.66 ± 0.43 | 6.97 ± 0.64 |

*)comparison example

The results prove the very good mechanical properties of the composite with the monomer MAMMA according to the invention as diluting monomer compared with a composite with the usual dental diluting monomer TEGDMA. A usual composite of an analogous composition in which, as diluting monomer, the bisacrylamide N,N'-diethyl-1,3-bis(acrylamido)-propane frequently used in dental materials was used produced composites with poorer mechanical properties. Composite A is particularly suitable as dental filling material.

The invention claimed is:
1. Dental material which comprises at least one compound of Formula I

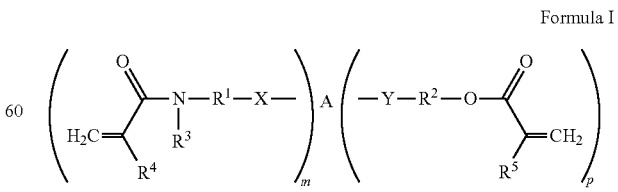

Formula I in which the variables have the following meanings:
A is an aliphatic linear or branched $C_1$-$C_{15}$ hydrocarbon radical which can be interrupted by one or more O;

X, Y independently of each other in each case are absent or are —NH—CO—O—, wherein X and Y are not absent at the same time, $R^1$, $R^2$ independently of each other in each case are absent or are an aliphatic linear or branched $C_1$-$C_{10}$ alkylene radical which can be interrupted by one or more O, wherein A, $R^1$ and $R^2$ together contain at least 3 C atoms, $R^3$ is an aliphatic linear $C_1$-$C_3$ alkyl radical, $R^4$, $R^5$ independently of each other in each case are hydrogen, methyl or ethyl, and m, p independently of each other in each case are an integer from 1 to 3.

2. Dental material according to claim 1, wherein the variables of Formula I have the following meanings:

A is an aliphatic linear or branched $C_1$-$C_8$ hydrocarbon radical which can be interrupted by one or more O, X is absent or is —NH—CO—O—, Y is absent or is —NH—CO—O—, wherein X and Y are not absent at the same time, $R^1$ is absent, $R^2$ is absent or is an aliphatic linear $C_1$-$C_2$ alkylene radical, $R^3$ is methyl or ethyl, $R^4$, $R^5$ independently of each other are hydrogen or methyl, and m, p independently of each other in each case are 1 or 2.

3. Material according to claim 1 which additionally comprises at least one radically polymerizable monomer for the radical polymerization.

4. Material according to claim 3 which comprises at least one multifunctional (meth)acrylate or a mixture of mono- and multifunctional (meth)acrylates.

5. Material according to claim 1 which comprises at least one filler.

6. Material according to claim 1 which comprises
a) 0.1 to 50 wt.-% of at least one compound of general formula I,
b) 0.01 to 10 wt.-% of at least one initiator,
c) 0 to 80 wt.-% other monomer(s),
d) 0 to 80 wt.-% filler(s) and
e) 0 to 70 wt.-% solvent,
in each case relative to the total mass of the material.

7. Material according to claim 6 for use as dental cement or dental filling composite which comprises
a) 0.1 to 40 wt.-% of at least one compound of general formula I,
b) 0.01 to 10 wt.-% of at least one initiator,
c) 0 to 50 wt.-% other monomer(s),
d) 10 to 80 wt.-% filler(s).

8. Material according to claim 6 for use as dental adhesive or coating material which comprises
a) 0.1 to 50 wt.-% of at least one compound of general formula I,
b) 0.01 to 10 wt.-% of at least one initiator,
c) 0 to 80 wt.-% other monomer(s),
d) 0 to 20 wt.-% filler(s),
e) 0 to 70 wt.-% solvents.

9. Material according to claim 6 for the manufacture of dental prostheses or artificial teeth which comprises
a) 0.1 to 50 wt.-% of at least one compound of general formula I,
b) 0.01 to 10 wt.-% of at least one initiator, and
c) 0 to 80 wt.-% other monomer(s),
d) 0 to 40 wt.-% filler(s).

10. Material according to claim 6 for the manufacture of inlays, onlays, crowns or bridges which contains
a) 0.1 to 50 wt.-% of at least one compound of general formula I,
b) 0.01 to 10 wt.-% of at least one initiator, and optionally
c) 0 to 60 wt.-% other monomer(s), and optionally
d) 10 to 80 wt.-% filler(s).

11. Material according to claim 1 for intraoral use to restore damaged teeth.

12. Material according to claim 11 for use as dental cement, dental filling composite, dental adhesive or veneering material.

13. Method of using the material according to claim 1 for the extraoral manufacture or repair of dental restorations.

14. Method of using the material according to claim 13 for the manufacture of artificial teeth, prostheses, inlays, onlays, crowns or bridges.

15. Material according to claim 3 which additionally comprises at least one initiator for the radical polymerization.

16. Material according to claim 6, which comprises
a) 1 to 40 wt.-% of at least one compound of general formula I,
b) 0.1 to 3.0 wt.-% of at least one initiator,
c) 0 to 60 wt.-% other monomer(s),
d) 0 to 80 wt.-% filler(s) and
e) 0 to 70 wt.-% solvent,
in each case relative to the total mass of the material.

17. Material according to claim 6, which comprises
a) 2 to 30 wt.-% of at least one compound of general formula I,
b) 0.1 to 3.0 wt.-% of at least one initiator,
c) 5 to 50 wt.-% other monomer(s),
d) 0 to 80 wt.-% filler(s) and
e) 0 to 70 wt.-% solvent,
in each case relative to the total mass of the material.

18. Material according to claim 7 for use as dental cement or dental filling composite which comprises
a) 1 to 30 wt.-% of at least one compound of general formula I,
b) 0.1 to 3.0 wt.-% of at least one initiator,
c) 0 to 40 wt.-% other monomer(s),
d) 20 to 80 wt.-% filler(s).

19. Material according to claim 7 for use as dental cement or dental filling composite which comprises
a) 5 to 30 wt.-% of at least one compound of general formula I,
b) 0.1 to 3.0 wt.-% of at least one initiator,
c) 5 to 40 wt.-% other monomer(s),
d) 30 to 80 wt.-% filler(s).

20. Material according to claim 8 for use as dental adhesive or coating material which comprises
a) 1 to 40 wt.-% of at least one compound of general formula I,
b) 0.1 to 3.0 wt.-% of at least one initiator,
c) 5 to 60 wt.-% other monomer(s),
d) 0 to 20 wt.-% filler(s),
e) 0 to 60 wt.-% solvents.

21. Material according to claim 8 for use as dental adhesive or coating material which comprises
a) 2 to 30 wt.-% of at least one compound of general formula I,
b) 0.1 to 3.0 wt.-% of at least one initiator,
c) 5 to 50 wt.-% other monomer(s),
d) 0 to 20 wt.-% filler(s),
e) 0 to 50 wt.-% solvents.

22. Material according to claim 8 wherein the solvents comprise water and/or ethanol.

23. Material according to claim 9 for the manufacture of dental prostheses or artificial teeth which comprises
   a) 1 to 40 wt.-% of at least one compound of general formula I,
   b) 0.1 to 3.0 wt.-% of at least one initiator, and
   c) 0 to 60 wt.-% other monomer(s),
   d) 0 to 40 wt.-% filler(s).

24. Material according to claim 9 for the manufacture of dental prostheses or artificial teeth which comprises
   a) 2 to 30 wt.-% of at least one compound of general formula I,
   b) 0.1 to 3.0 wt.-% of at least one initiator, and
   c) 5 to 50 wt.-% other monomer(s),
   d) 0 to 40 wt.-% filler(s).

25. Material according to claim 10 for the manufacture of inlays, onlays, crowns or bridges which contains
   a) 1 to 40 wt.-% of at least one compound of general formula I,
   b) 0.1 to 3.0 wt.-% of at least one initiator, and optionally
   c) 0 to 50 wt.-% other monomer(s), and optionally
   d) 15 to 80 wt.-% filler(s).

26. Material according to claim 10 for the manufacture of inlays, onlays, crowns or bridges which contains
   a) 2 to 30 wt.-% of at least one compound of general formula I,
   b) 0.1 to 3.0 wt.-% of at least one initiator, and optionally
   c) 5 to 50 wt.-% other monomer(s), and optionally
   d) 20 to 80 wt.-% filler(s).

\* \* \* \* \*